United States Patent
Narayanan

[11] Patent Number: 5,486,357
[45] Date of Patent: * Jan. 23, 1996

[54] RADIOFREQUENCY PLASMA BIOCOMPATIBILITY TREATMENT OF INSIDE SURFACES

[75] Inventor: Pallassana V. Narayanan, Davie, Fla.

[73] Assignee: Cordis Corporation, Fla.

[ * ] Notice: The portion of the term of this patent subsequent to Sep. 14, 2010, has been disclaimed.

[21] Appl. No.: 143,994

[22] Filed: Oct. 27, 1993

Related U.S. Application Data

[63] Continuation of Ser. No. 4,998, Jan. 15, 1993, abandoned, which is a continuation of Ser. No. 720,410, Jun. 25, 1991, Pat. No. 5,244,654, which is a continuation-in-part of Ser. No. 610,548, Nov. 8, 1990, Pat. No. 5,132,108.

[51] Int. Cl.$^6$ .......................... A61L 33/00; A61L 29/00; A61K 31/725; A61K 35/62; B05D 3/06

[52] U.S. Cl. ................ 424/78.17; 424/422; 424/423; 427/535; 427/536; 427/539; 427/2.3; 427/238; 525/54.1; 525/54.2; 525/406; 525/423; 525/424; 525/430; 525/449; 525/453; 525/454; 525/474; 525/937; 604/96; 604/239; 210/500.24; 522/915; 523/112; 530/816

[58] Field of Search ................. 424/78.17, 422, 424/423; 427/535, 536, 539; 210/500.24

[56] References Cited

U.S. PATENT DOCUMENTS

| | | | |
|---|---|---|---|
| 4,131,691 | 12/1978 | Morley et al. | 427/41 |
| 4,261,806 | 4/1981 | Asai et al. | 204/165 |
| 4,266,999 | 5/1981 | Baier | 156/227 |
| 4,326,532 | 4/1982 | Hammar | 128/349 R |
| 4,613,517 | 9/1986 | Williams et al. | 427/2 |
| 4,632,842 | 12/1986 | Karwoski et al. | 427/2 |
| 4,656,083 | 4/1987 | Hoffman et al. | 428/265 |
| 4,678,671 | 7/1987 | Feijen et al. | 424/443 |
| 4,692,347 | 9/1987 | Yasuda | 427/40 |
| 4,846,101 | 7/1989 | Montgomery et al. | 118/723 |
| 4,948,628 | 8/1990 | Montgomery et al. | 427/39 |
| 5,132,108 | 7/1992 | Narayanan et al. | 424/78.17 |
| 5,244,654 | 9/1993 | Narayanan | 424/78.17 |

*Primary Examiner*—Edward J. Webman
*Attorney, Agent, or Firm*—Lockwood, Alex, Fitzgibbon & Cummings

[57] ABSTRACT

Internal polymeric surfaces of medical devices are provided that have enhanced biocompatibility properties. The internal polymeric surface presents an anti-thrombogenic, fibrinolytic or thrombolytic interface with body fluids such as blood flowing through medical device tubing during implantation for medical procedures. The biocompatibility enhancing agent is secured to the polymeric substrate by a spacer molecule which is covalently bound to the internal polymeric surface which had been subjected to radiofrequency plasma treatment with a low pressure plasma medium of water vapor, oxygen or combination of water vapor and oxygen gas.

15 Claims, 4 Drawing Sheets

RADIOFREQUENCY PLASMA BIOCOMPATIBILITY TREATMENT OF INSIDE SURFACES

This application is a continuation of application Ser. No. 004,998, filed Jan. 15, 1993, which is a continuation of Ser. No. 720,410, filed Jun. 25, 1991, now U.S. Pat. No. 5,244,654, which is a continuation-in-part of application Ser. No. 610,548, filed Nov. 8, 1990, now U.S. Pat. No. 5,132,108.

BACKGROUND AND DESCRIPTION OF THE INVENTION

The present invention generally relates to enhancing the biocompatibility of partially enclosed interior polymeric surfaces of medical devices such as tubing for catheters and the like. More particularly, the invention relates to surface activation of polymeric surfaces such as lumens of medical-grade tubing by radiofrequency plasma treatment as a step in achieving immobilization of anti-thrombogenic agents or the like onto interior polymeric surfaces. The radiofrequency plasma medium is at a substantially low pressure and includes water vapor, oxygen or combinations thereof. When this medium is subjected to radiofrequency plasma discharge conditions, the polymeric surfaces of the device being treated, including partially enclosed interior surfaces such as lumens, are activated for attachment thereto of anti-thrombogenic agents such as heparinous materials and the like.

It is well known that many medical devices must have surfaces which are of enhanced biocompatibility. It is also well-known that, generally speaking, biocompatibility properties are enhanced by attempting to secure anti-thrombogenic agents to polymeric surfaces of medical devices, particularly those which are blood-contacting surfaces to be implanted or otherwise used during medical procedures and the like. In many instances, it is particularly undesirable to have the anti-thrombogenic agent leach away in wet environments such as are encountered by medical devices that engage blood or other body fluids. At times, these surfaces in need of biocompatibility enhancement are partially enclosed interior surfaces such as lumens of catheters or other medical tubing.

Certain attempts have been made and approaches have been suggested whereby a polymeric surface is activated by treatment with a plasma which in turn reacts with heparin or the like to provide a polymeric surface having anti-thrombogenic properties. Included are patents incorporating plasma discharge treatment with a gaseous environment having a variety of gases, including inert gases and organic gases. Patents in this regard include U.S. Pat. Nos. 4,613,517, 4,656,083 and 4,948,628, which mention a variety of plasma media including those generated from hydrogen, helium, ammonia, nitrogen, oxygen, neon, argon, krypton, xenon, ethylenic monomers and other hydrocarbons, halohydrocarbons, halocarbons and silanes. It will be appreciated that various ones of these plasma media are relatively expensive and can be hazardous to use within a manufacturing environment and/or to dispose of as waste. Also, certain plasma media are more suitable for treatment of specific substrates.

It is desirable to provide a surface treatment procedure which is available for use in connection with rendering anti-thrombogenic any of a number of surfaces of medical devices or the like, including partially enclosed interior surfaces. It is further desirable that any plasma deposition procedure included in this regard avoid the need to use plasma media that are expensive, potentially hazardous or otherwise difficult to handle. At the same time, any plasma media should strongly bind the anti-thrombogenic agent to the surface being treated, preferably while also accomplishing this in an especially efficient manner that is readily susceptible to use on a large scale.

While certain approaches have been suggested which are particularly designed for treating interior surfaces, these typically require specifically designed equipment and/or are not particularly useful for treating interior surfaces which are spaced a relatively long distance from the access opening to the interior surface. This situation would occur, for example, in attempting to treat a long length of small-diameter tubing such as that for an angiographic or angioplasty catheter, particularly when it is important that entire length of the tubing, including the internal surface at the mid-length of the tubing, is to be treated. In addition to the patents mentioned hereinabove, the following patents describe devices for treating surfaces such as the inside of a tubular body: U.S. Pat. Nos. 4,261,806, 4,692,347 and 4,846,101.

It has been discovered that plasma media which include a substantial concentration of water vapor or oxygen, either alone or in combination with each other, and when provided at especially low pressures, achieve especially advantageous activation of partially enclosed interior surfaces such as the lumen of an elongated, small diameter tubing, when the low-pressure plasma medium is subjected to radiofrequency plasma treatment conditions. The thus activated surface is preferably treated with a spacer component having amine moieties, particularly spacer components which have primary or secondary amine groups. An anti-thrombogenic agent or the like, typically with the assistance of a coupling agent, is covalently bound to the spacer component. The result is an evenly covered biocompatible surface that significantly avoids leaching of the anti-thrombogenic agent or the like out of the partially enclosed interior surface such as the tubing lumen.

It is accordingly a general object of the present invention to provide an improved method for treating interior polymeric surfaces and medical devices or the like having such surfaces.

Another object of this invention is to provide improved medical device components such as tubing having internal polymeric surfaces with anti-thrombogenic agents or the like immobilized thereon.

Another object of the present invention is to provide an improved anti-thrombogenic interior polymeric surface and method of making same which utilizes radiofrequency plasma discharge techniques that avoid the use of expensive or hazardous plasma media and that avoid the need for specifically designed plasma treatment equipment.

Another object of this invention is to provide an improved method for covalently binding anti-thrombogenic agents or the like to substantially enclosed polymeric surfaces, which agents do not leach away in wet environments, as well as to the improved substantially enclosed polymeric surfaces thus produced.

Another object of the present invention is to provide an improved process for rendering interior surfaces of medical device components, such as narrow tubing, anti-thrombogenic through a process by which the mean free path of the gaseous treatment media generally approximates the dimensions of the interior volume such as the inside diameter of medical grade tubing, whereby the reactive Species are able to penetrate the inside volume of the device before they become deactivated in the gaseous phase.

These and other objects, features and advantages of this invention will be clearly understood through a consideration of the following detailed description.

DESCRIPTION OF THE PARTICULAR EMBODIMENTS

Figure 1:
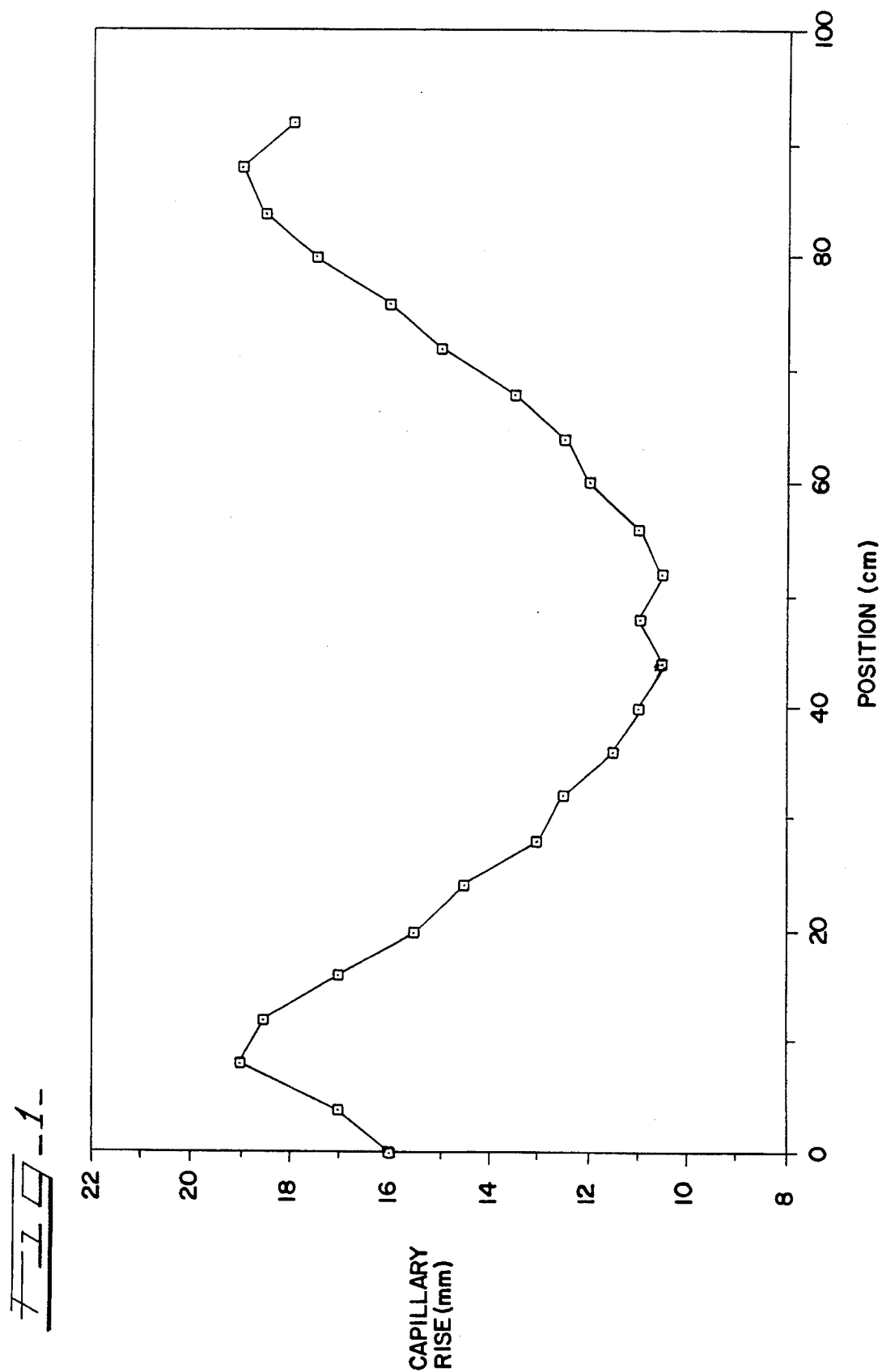
FIG. 1 demonstrates the results of Example 1.

The present invention is particularly suitable in connection with the treatment of interior surfaces of medical device articles having interior surfaces which are not easily contacted, such as mid-length interior surfaces of medical device tubing having an especially small internal diameter. Specific medical device articles which are advantageously treated according to the invention include catheters, cannulas, angioplasty balloon catheters and the like and any other devices having operational requirements and properties that can be improved by attaching an anti-thrombogenic, fibrinolytic or thrombolytic agent to one or more surfaces of the device. Typically these types of devices or at least the internal surfaces thereof are made of polymeric materials. In the event that the surface to be treated in accordance with this invention is made of some other material, a thin layer of a suitable polymeric material first can be applied to the surface to be treated.

Polymers which are suitable for use as the surface to be modified with an anti-thrombogenic agent or the like in accordance with the present invention include various polyurethane components such as polyurethanes and polyurethane copolymers such as Pellethane Polymers. Included are polyurethane-polyester copolymers, polyurethane-polyether copolymers and nylon-polyether copolymers such as Vestamid. Other polymers which can be treated according to the invention include Silastic (silicon rubber), nylons and other polyamides, nylon-polyester copolymers, polyolefins such as high density polyethylene and the like. The selected polymer must have overall properties which, except for thrombus concerns, render the polymers suitable for the interior surface of a medical device made in accordance with the present invention.

In accordance with the invention, these types of interior polymeric surfaces are made more suitable for long-term or short-term contact with flowing blood or other body fluids. This is accomplished by attaching an anti-thrombogenic agent, fibrinolytic agent or thrombolytic agent to the interior surface. These agents are used in relatively small amounts, and they are attached in such a manner that they remain biologically active, while at the same time being affixed to the polymeric surface in so secure a manner that the agents will not leach away in wet in vitro or in vivo environments.

Securement of the anti-thrombogenic agent or the like onto the polymeric interior surface includes positioning the tubing or the like having the interior polymeric surface within an apparatus to provide a radiofrequency plasma discharge environment. Devices for providing such an environment are generally known in the art. Typical devices in this regard are shown, for example, in U.S. Pat. Nos. 4,632,842 and 4,656,083, the subject matter thereof being incorporated by reference hereinto. In devices used according to this invention, a reactor chamber is provided, and the device having the internal surface to be treated is simply inserted into the chamber without requiring any special structures or positioning. The chamber is evacuated by a suitable vacuum pump or the like, typically to a pressure below the treatment pressure targeted for the radiofrequency plasma discharge.

A source of fluid which provides the plasma environment is fed into the evacuated chamber, and the desired treatment pressure for the plasma medium is maintained. Glow discharge is induced within the reactor chamber by an electrode assembly disposed about the chamber. For example, when the chamber is generally cylindrically shaped, the electrode assembly can include a pair of band electrodes that are mounted on a traveling block which moves along a desired length of the reactor chamber. The electrode assembly can include instead a radiofrequency coil or the like. After the flow of treating medium or fluid has been established at the desired pressure, discharge is initiated by generating a radiofrequency electric field within the reactor chamber, thereby inducing treatment of the interior polymeric surface. The radiofrequency electric field can be applied to the chamber either capacitively or inductively.

In accordance with the present invention, the treating fluid or plasma medium is provided within the chamber. When the radiofrequency electric field is applied to this plasma medium, reactive species are created. The reactive species, when they encounter the polymeric surface, react with atoms and/or molecules of the polymeric material, thereby modifying the chemical nature of the surface. It is believed that the polymeric surface is modified by causing the formation of carbon groups and/or hydroxyl groups on the surface of the polymeric material. Provided the needed low pressure conditions are maintained, the interior polymeric surface will thus be treated.

With more particular reference to the treating fluid or plasma medium, air or other gas is first evacuated from the radiofrequency treatment chamber until virtually no air or other gas remains therewithin. Then the water vapor or oxygen is pumped or otherwise injected into the chamber. It is also possible to mix the oxygen with the water and/or water vapor, which can further enhance the efficiency of the surface modification carried out in accordance with this aspect of the invention. The atmosphere within the chamber can be 100% water vapor or 100% oxygen, based upon the total volume of the fluid within the chamber. When water vapor and oxygen are mixed, the mixture can have as low as about 40% by volume of water vapor. When water vapor and oxygen are included in the plasma gas within the chamber, the preferred volume of water vapor is between about 40 and about 90 volume percent, with the balance being oxygen. It will be appreciated by those familiar with plasma discharge techniques that these volume percents are as present within the chamber at any instant in time because these are flowing fluids.

Concerning the treating fluid or plasma medium to be maintained during radiofrequency plasma surface modification procedures, the pressure should not exceed about 0.25 Torr, typically less than about 0.2 Torr. Generally speaking, the plasma gas pressure will be no lower than 0.01 Torr. Preferably, the treatment pressure should be maintained below about 0.1 Torr. At these reduced pressures, an average gaseous molecule will travel longer before it encounters another gaseous molecule. In gaseous kinetics, this is referred to as the mean free path. This longer mean free path at reduced pressures results in increased diffusion length of the reactive species, as well as of other species in the plasma species. If the dimension of a confined volume, such as the diameter of a tubing, is comparable to the mean free path of the reactive species, there is a much higher probability that the reactive species entering within the interior surface will collide with the wall of the device rather than undergo a gas phase collision. These wall collisions cause the inside surface to be chemically functionalized as required by the present invention.

These specific conditions can be used to deposit thin film on the inside surfaces using depositing monomers as plasma media. By the procedure according to the invention, the internal surfaces or lumens of tubings having an internal diameter of 0.072 inch or lower and a length of up to about 4 feet is successfully treated. Often such tubings are used as catheters for diagnostic and interventional purposes. For example, the tubing can have a lumen diameter of less than about 0.1 inch and have a length suitable for use as a catheter for diagnostic or interventional uses. Generally speaking, treatment of tubing of this general size and within uncomplicated equipment is successfully carried out within about 10 to 30 minutes within an operating pressure range of between about 0.04 Torr and about 0.1 Torr.

When a polymeric surface such as Silastic (silicone rubber) is to be treated with the water vapor, oxygen or water vapor/oxygen plasma, it is preferred to pretreat the silicone rubber surface. A suitable pretreatment is within an inert gas plasma such as argon and the like. Suitable reactive species are formed thereafter with the water vapor, oxygen or water vapor and oxygen plasma as discussed herein. The resulting reactive species-modified polymeric surface is then treated with a spacer molecule which provides reactive sites for attachment of the anti-thrombogenic agent or the like thereto and thus to the polymeric surface. Preferred spacer molecules are those which contain primary or secondary amine groups. Exemplary molecules having suitable spacer groups include albumin, streptokinase, urokinase, polyethyleneimine (PEI) and the like, and combinations thereof.

Covalent linkages between the reactive sites (typically carboxyl groups or hydroxyl groups) on the functionalized polymeric surface and the amine groups of the spacer molecule are formed. Generally speaking, the covalent linkages are accomplished by a condensation or trans-esterification reaction therebetween, often while using a suitable coupling agent. Typical coupling agents in this regard include 1-ethyl-3-(3-dimethylaminopropyl)carbodiimide hydrochloride (EDC), dicyclohexyl carbodiimide (DCC) or other known coupling agents and the like.

The spacer components are typically applied in solution form. For example, a spacer component such as polyethyleneimine can be utilized within a water solution containing approximately one percent by weight of PEI. Typically, the spacer component will be present at a concentration of between about 1.0 and about 5.0 weight percent, based upon the weight of the spacer solution.

A suitable anti-thrombogenic, fibrinolytic or thrombolytic agent is then covalently bound to the spacer group, also by means of condensation or transesterification chemistry. It is preferred that the agent exhibit acid functionality, whereby the carboxyl groups form a covalent linkage with amine groups of the spacer component. The resultant device has an anti-thrombogenic internal surface from which the anti-thrombogenic agent does not readily leach.

Exemplary anti-thrombogenic agents include heparinous components such as heparin, hirudin, heparin-albumin conjugates, hyaluronic acid, and the like. Illustrative fibrinolytic or thrombolytic agents include streptokinase, urokinase, and the like. Combinations of spacer component and of anti-thrombogenic agent or the anti-thrombogenic agent by itself can be used in the anti-thrombogenic agent composition which is attached to the modified polymeric surface having reactive sites. The anti-thrombogenic agent or the like is applied in the form of a solution having between about 10 and about 20 weight percent of anti-thrombogenic, fibrinolytic or thrombolytic agent, based upon the total weight of the composition.

The following examples illustrate the process and product, as well as performance results.

EXAMPLE 1

Nylon 12 tubing having an inner diameter of 0.055 inch and a length of 39 inches was treated in a tubular radiofrequency plasma reactor. The plasma was created in the tubular chamber by capacitively coupling the RF atone end of the tubular reactor so that the visible part of the plasma was confined to one end of the tubing. Oxygen was the plasma medium. It was present at a pressure of 0.07 Torr, and the treatment proceeded for 15 minutes at 20 watts of power. A pressure regulator was present at the downstream portion of the device in order to control the flow of gases and to maintain the desired plasma gas pressure within the reactor. Treatment was effective without requiring any specific orientation of the tubing being treated within the reactor. After treatment was completed, the treated tubing was removed from the reactor and tested to determine the extent of treatment throughout the lumen thereof. The 39 inch tubing was cut into 25 tubing pieces, each 4 cm in length. Each length was numbered 1 through 25 starting from one end to the other. Each piece was dipped into a beaker of de-ionized water. The height to which water moved within the lumen of each piece indicated the extent of surface functionalization that enhanced capillary rise when compared with a surface such as one that had not been subjected to any treatment. Thus, each piece of the tubing was able to support a column of water whose height was a function of the surface energy of the inside surface and thus an indication of the degree to which the inside surface had been functionalized by the radiofrequency plasma.

FIG. 1 plots the capillary rise for each 4 cm length of tubing, the plot being in order along the length of tubing prior to severance and at the time of its treatment. It will be appreciated that FIG. 1 indicates there was a gradient of treatment effect from the ends to the center of the tubing. The treatment of even the central-most 4 cm lengths was found to be adequate to attach an anti-thrombogenic agent to the lumen thereof.

EXAMPLE 2

Figure 2:
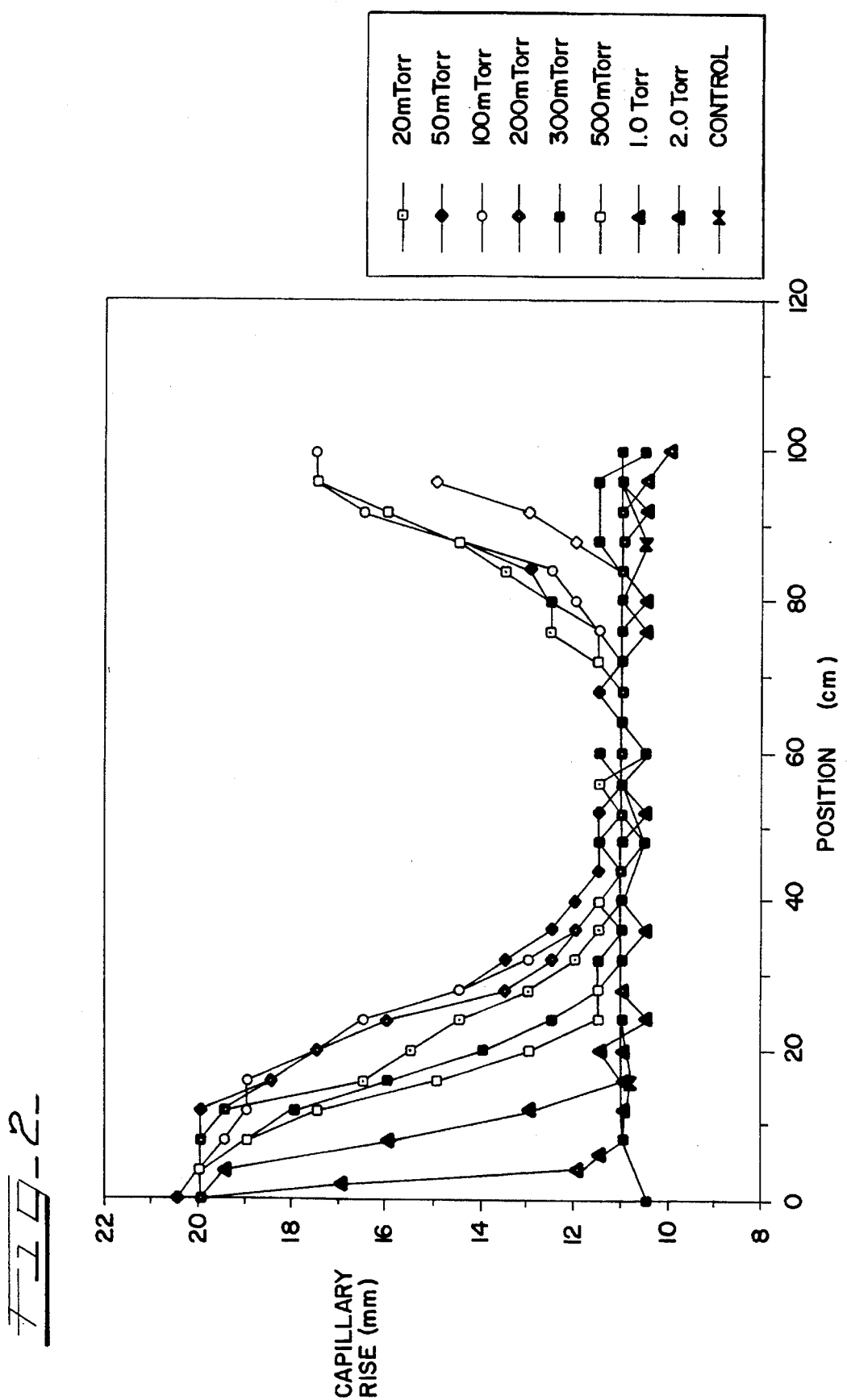
FIG. 2 demonstrates the results of Example 2.

The procedure of Example 1 was substantially repeated at different various operating pressures and under the same one-end plasma arrangement under 20 watts of power. FIG. 2 is a plot which indicates the effect of operating pressure for constant treatment time, plotting capillary rise versus position along the length of tubing prior to severance. The areas which received minimal treatment were at and near the midpoint along the length of the tubing. It will be appreciated from these data that, as the pressure of operation is reduced, the gradient becomes smaller indicating that the treatment length becomes longer. The central areas which received minimal treatment were more extensive or longer at the higher pressures than at the lower pressures, as can be seen in FIG. 2. The control plot is of a totally untreated Nylon 12 tube which was subjected to the capillary test.

EXAMPLE 3

Figure 3:
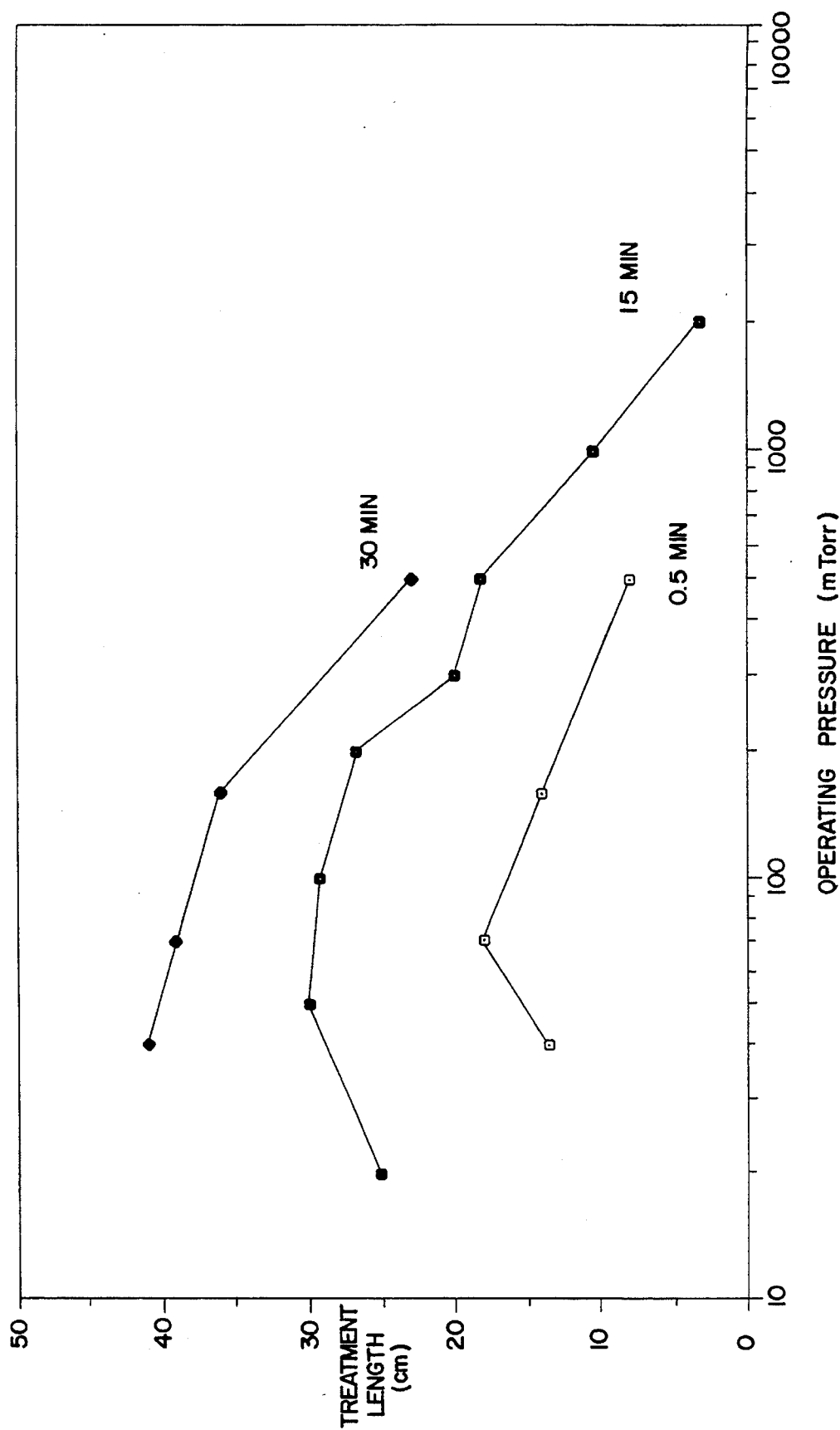
FIG. 3 demonstrates the results of Example 3.

Tests were conducted as described in Example 1, this time varying the operating pressure. The change of treatment length as a function of operating pressure data are reported in FIG. 3. In this Figure, the length of the treated tubing at which the capillary rise is 3 mm above the control value is plotted as a function of the operating pressure for different treatment times. The control sample had a capillary rise value of 10.3±0.3 mm. The power applied was constant, and three different treatment times were utilized, as reported in FIG. 3.

EXAMPLE 4

Figure 4:
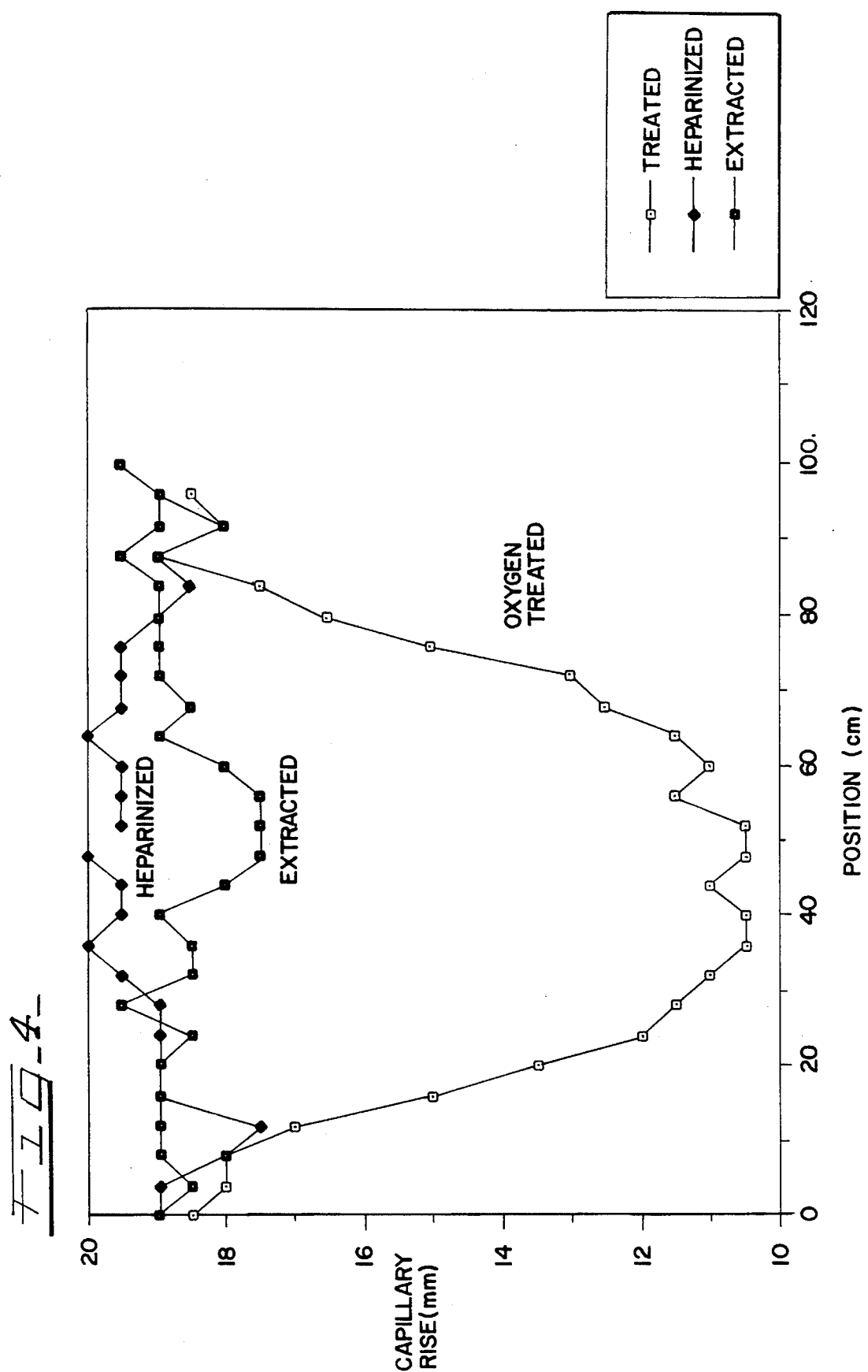
FIG. 4 demonstrates the results of Example 4.

Tubing as described in Example 1 was subjected to radiofrequency plasma deposition from an oxygen medium. The treatment was carried out within a commercial reactor, a Model 7104 unit of Branson International Plasma Corporation. This commercial equipment included seven trays, and the tubing was laid upon the trays for treatment according to the invention. The control sample had a capillary rise value of 10.3±0.3 mm. The treatment pressure in the radiofrequency reactor was about 230 milliTorr. The thus modified tubing was then treated with a spacer molecule, followed by attachment of heparin. Thereafter, the surface of the tubing, both inside and outside, was stained with toluidine blue dye to check for the presence of heparin. The dye turned purple indicating the presence of heparin. The heparinized surface was extracted in phosphate buffered saline for at least 72 hours to determine whether or not it was bound to the surface. After 72 hours in the phosphate buffered saline, when the heparinized surface was stained with toluidine blue, the change of dye color to purple indicated that heparin was still present on the surface. The presence of heparin was also confirmed by another independent surface analytic technique, namely static secondary ion mass spectroscopy. This illustrates that the bound heparin was immobilized on the surface. The heparinized surface possessed a high surface energy due to the various hydrophilic functional groups in heparin molecule. This was evident in the capillary rise measurements of the heparinized tubing. FIG. 4 plots the capillary rise data for the radiofrequency plasma treated sample, as well as for the heparinized sample and the extracted sample. A flat capillary rise profile is evident for the heparinized sample, which indicates that adequate heparin is present even along the middle length of the tubing's lumen. The relatively flat profile for the extracted sample indicates that the heparin was not extracted to any substantial degree.

EXAMPLE 5

Tubing for use as catheters for diagnostic and interventional purposes was treated as described in Example 1, except for the following differences. The tubing was a nylon-polyester copolymer (Vestamid). The plasma medium was a mixture of water and oxygen at a pressure of 0.090 Torr. The treated surface was heparinized, both on the outside and in the lumen. Positive test results indicated the immobilization of heparin on both surfaces.

EXAMPLE 6

High density polyethylene tubing having an internal diameter of 0.051 inch and a length of 12 inches was treated in a water vapor plasma for 10 minutes at a pressure of 0.1 Torr and under 20 watts of radiofrequency power. The thus treated tubing was treated both on the outside and within the lumen with heparin. Both surfaces were then tested for the presence of heparin as described in Example 4, the tests positively indicating the presence of heparin.

EXAMPLE 7

Tubing of the type described in Example 6 was treated in a radiofrequency plasma containing a medium of a mixture of water and oxygen at a pressure of 0.1 Torr. The power supply was set at 20 watts. Heparinization followed, and the heparinized surfaces were tested, thereby indicating the presence of immobilized heparin within the lumen as well as on the outside surface of the tubing.

EXAMPLE 8

Nylon 12 tubing having the size specified in Example i was treated in radiofrequency plasma using the same process conditions as in Example 1. In this Example 8, the two ends of the tubing were looped into 360 degree loops and into an ellipsoidal shape. The treated samples were tested in accordance with the capillary rise techniques discussed hereinabove. The results were comparable to those for straight elongated tubing, thereby indicating that the ends of the tubing need not be straight for the treatment to be effective within the lumen, provided the low pressure processing according to the present invention is achieved. In fact the treatment effects in the looped and shaped samples were as good as that in straight tubing. This is important in view of the need to treat lumens of catheters which have shapes other than straight tubings. Often catheters have curved portions, especially at their end tip portions.

It will be understood that the embodiments of the present invention which have been described are illustrative of some of the applications of the principles of the present invention. Numerous modifications may be made by those skilled in the art without departing from the true spirit and scope of the invention.

I claim:

1. A method for enhancing the biocompatibility of interior polymeric surfaces of medical device components, comprising the steps of:

positioning a medical device component within a radiofrequency plasma discharge apparatus, the medical device component being catheter tubing with a polymeric surface interior lumen having a diameter of less than about 0.1 inch, said catheter tubing having a length suitable for use as a catheter in humans;

providing a reduced pressure environment within the radiofrequency plasma discharge apparatus, said reduced pressure environment being about 0.25 Torr or less;

inserting into said reduced pressure environment a plasma medium selected from the group consisting of water vapor, oxygen gas, and mixtures thereof, said plasma medium having a pressure of less than about 0.2 Torr;

subjecting said plasma medium to a radiofrequency electric field to induce a gas discharge in order to form reactive species from said plasma medium within the plasma discharge apparatus and within the lumen to form a modified interior polymeric lumen surface comprising reactive sites which had been modified by the subjecting step, said subjecting step being carried out for at least about 10 minutes and while said plasma medium has a pressure of less than about 0.2 Torr;

treating said modified interior polymeric lumen surface with a spacer component having amine groups whereby covalent linkages are formed between the spacer component amine groups and the reactive sites of the modified interior polymeric lumen surface to form a spacer component-treated modified polymeric lumen surface; and covalently bonding an anti-thrombogenic, fibrinolytic or thrombolytic agent having acid functionality and biologically active properties to said spacer component-treated modified polymeric lumen surface, whereby said modified polymeric lumen surface is rendered into a biocompatible surface, and the anti-thrombogenic, fibrinolytic or thrombolytic agent of the biocompatible surface is resistant to extraction under in vivo conditions while retaining its biologically active properties.

2. The method in accordance with claim 1, wherein said plasma medium includes between about 40 to about 90 volume percent water vapor and between about 10 and about 60 volume percent oxygen, based upon the total volume of the plasma medium.

3. The method in accordance with claim 1, wherein said treating step utilizes a spacer component selected from the group consisting of primary amines, secondary amines, and mixtures thereof.

4. The method in accordance with claim 1, wherein said interior polymeric lumen surface modified by said subjecting step includes reactive sites of carboxyl groups, hydroxyl groups or mixtures thereof.

5. The method in accordance with claim 1, wherein said treating step is carried out in the presence of a coupling agent.

6. The method in accordance with claim 1, wherein said contacting step contacts said spacer component-treated modified polymeric surface with a heparinous material.

7. The method in accordance with claim 1, wherein said subjecting step is carried out while said plasma medium has a pressure of less than about 0.1 Torr.

8. The method in accordance with claim 1, wherein the catheter tubing in said positioning step has a lumen diameter of about 0.072 inch or less.

9. A medical device component having a biocompatible polymeric surface, wherein said medical device component is catheter tubing, said catheter tubing having a lumen with a diameter of less than about 0.1 inch and having a length suitable for use as a catheter in humans, and said biocompatible polymeric surface comprises an interior polymeric lumen surface which has been modified by subjecting the interior polymeric lumen surface to radiofrequency discharge treatment within a low-pressure plasma medium for at least about 10 minutes to provide a treated interior polymeric lumen surface, the plasma medium selected from the group consisting of water vapor, oxygen gas, and mixtures thereof, said plasma medium having a pressure of less than about 0.2 Torr, followed by treatment of the treated interior polymeric lumen surface with a spacer component having amine groups forming covalent linkages with the treated interior polymeric lumen surface to form a spacer component-treated interior polymeric lumen surface, after which an anti-thrombogenic, fibrinolytic or thrombolytic agent having acid functionality has been covalently bonded to the spacer component-treated interior polymeric lumen surface to provide a biocompatible partially enclosed interior polymeric lumen surface.

10. The medical device component in accordance with claim 9, said polymeric surface is a polyurethane, a polyurethane copolymer, a nylon, a polyamide or a silicone rubber polymer.

11. The medical device component in accordance with claim 9, wherein the medical device component is a component of a catheter, a cannula or a balloon catheter.

12. The medical device component in accordance with claim 9, wherein said covalent linkages between the modified polymeric lumen surface and the spacer component are between carboxyl or hydroxyl groups formed by the radiofrequency discharge treatment on the polymeric surface and primary or secondary amine groups of the spacer component.

13. The medical device component in accordance with claim 12, wherein a covalent linkage is present between primary or second amine groups of spacer component molecules and the acid functionality groups of the anti-thrombogenic, fibrinolytic or thrombolytic agent.

14. The medical device component in accordance with claim 9, wherein said diameter of the catheter tubing lumen is about 0.072 inch or less.

15. The medical device in accordance with claim 9, wherein said plasma medium has a pressure of less than about 0.1 Torr.

* * * * *

UNITED STATES PATENT AND TRADEMARK OFFICE
CERTIFICATE OF CORRECTION

PATENT NO. : 5,486,357
DATED : January 23, 1996
INVENTOR(S) : Pallassana V. Narayanan It is certified that error appears in the above-indentified patent and that said Letters Patent is hereby corrected as shown below:

Col. 2, line 67, "Species" should read --species--.
Col. 3, line 39, "Polymers" should read --polymers--; line 59, "in vitro" and "in vivo" should be in italics.
Col. 4, line 33, "carbon" should read --carboxyl--.
Col. 5, line 10, "film" should read --films--; line 46, insert a hyphen between "1-ethyl-3-(3-dimethylaminopropyl)" and "carbodiimide".
Col. 6, line 19, "atone" should read --at one--.
Col. 8, line 18, "i" should read --1--.
Col. 9, line 15, "in vivo" should be in italics; line 18, "40 to" should read --40 and--.
Col. 10, line 20, after "claim 9," insert --wherein--.

Signed and Sealed this

Eighth Day of October, 1996

Attest:

BRUCE LEHMAN

*Attesting Officer*     *Commissioner of Patents and Trademarks*